(12) United States Patent
Xu et al.

(10) Patent No.: US 12,269,039 B2
(45) Date of Patent: Apr. 8, 2025

(54) BIOCHEMICAL REACTION TEST TUBE AND USE METHOD THEREOF, AND GENE AMPLIFICATION KIT

(71) Applicants: QUICKING BIOTECH CO., LTD., Shanghai (CN); QUICKING BIOENGINEERING CO., LTD., Shanghai (CN)

(72) Inventors: Xianghua Xu, Shanghai (CN); Xiaoming He, Shanghai (CN); Zhongren Zhou, Shanghai (CN); Lei Zhang, Shanghai (CN)

(73) Assignees: QUICKING BIOTECH CO., LTD., Shanghai (CN); QUICKING BIOENGINEERING CO., LTD., Shanghai (CN)

( * ) Notice: Subject to any disclaimer, the term of this patent is extended or adjusted under 35 U.S.C. 154(b) by 897 days.

(21) Appl. No.: 17/310,806

(22) PCT Filed: Feb. 25, 2020

(86) PCT No.: PCT/CN2020/076666
§ 371 (c)(1),
(2) Date: Aug. 25, 2021

(87) PCT Pub. No.: WO2020/173445
PCT Pub. Date: Sep. 3, 2020

(65) Prior Publication Data
US 2022/0088591 A1  Mar. 24, 2022

(30) Foreign Application Priority Data

Feb. 25, 2019  (CN) .................. 201920239379.X
Feb. 23, 2020  (CN) .................. 202010110246.X (51) Int. Cl.
*B01L 3/00* (2006.01)
*B01L 7/00* (2006.01)
*C12Q 1/686* (2018.01)

(52) U.S. Cl.
CPC ............. *B01L 3/50825* (2013.01); *B01L 7/52* (2013.01); *C12Q 1/686* (2013.01);
(Continued)

(58) Field of Classification Search
CPC ......... B01L 2200/0689; B01L 2300/04; B01L 2300/1805; B01L 3/5082; B01L 3/50825;
(Continued)

(56) References Cited

U.S. PATENT DOCUMENTS 4,106,907 A * 8/1978 Charlton .................. G01T 7/02
436/817
2003/0162285 A1 * 8/2003 Tajima ................ B01L 3/50851
435/303.1
(Continued)

FOREIGN PATENT DOCUMENTS

CN  103103118 A  5/2013
CN  103243087 A  8/2013
(Continued)

OTHER PUBLICATIONS

Phaneuf et al ("Thermally multiplexed polymerase chain reaction"). Biomicrofluidics Jul. 1, 2015; 9 (4): 044117. (Year: 2015).*

*Primary Examiner* — Jennifer Wecker
*Assistant Examiner* — Jonathan Bortoli
(74) *Attorney, Agent, or Firm* — Ziegler IP Law Group, LLC.

(57) ABSTRACT

The present application relates to a biochemical reaction test tube and a use method thereof, and a gene amplification kit. The biochemical reaction test tube includes a tube portion and a cover portion. The tube portion includes: a tube body including a first chamber and a second chamber, where a
(Continued)

bottom of the second chamber is spaced apart from a bottom of the first chamber; and a limit unit provided at an outer side of the tube body. The first chamber and the second chamber are provided at different heights and used to hold different reaction components and solutions. Only one of the first chamber and the second chamber is heated to complete a biochemical reaction. When the test tube is vertically flipped at 180° and shaken, the solutions in the first chamber and the second chamber are mixed to further achieve a reaction, which eliminates harmful results.

16 Claims, 8 Drawing Sheets

(52) U.S. Cl.
CPC ............... *B01L 2200/0689* (2013.01); *B01L 2300/04* (2013.01); *B01L 2300/1805* (2013.01)

(58) Field of Classification Search
CPC ............... B01L 7/52; B01L 2300/043; B01L 2300/047; C12Q 1/686; C12Q 2563/107
See application file for complete search history.

(56) References Cited

U.S. PATENT DOCUMENTS

| | | | |
|---|---|---|---|
| 2004/0110167 A1* | 6/2004 | Gerdes | C12Q 1/6834 436/514 |
| 2004/0223874 A1* | 11/2004 | Numajiri | B01L 3/502761 422/400 |
| 2005/0123457 A1* | 6/2005 | Tajima | G01N 21/03 422/400 |
| 2010/0248245 A1* | 9/2010 | Ying | G01N 21/03 435/6.1 |
| 2011/0031252 A1* | 2/2011 | Pack | B01L 3/5025 220/507 |
| 2019/0250075 A1* | 8/2019 | Wu | A61B 10/0051 |

FOREIGN PATENT DOCUMENTS

| | | |
|---|---|---|
| CN | 103267839 A | 8/2013 |
| CN | 103278625 A | 9/2013 |
| CN | 104293659 A | 1/2015 |
| CN | 105836240 A | 8/2016 |

* cited by examiner

BIOCHEMICAL REACTION TEST TUBE AND USE METHOD THEREOF, AND GENE AMPLIFICATION KIT

CROSS REFERENCE TO RELATED APPLICATION(S)

This patent application is a national stage application of PCT/CN2020/076666 filed on Feb. 25, 2020, which claims the benefit and priority of Chinese Patent Application No. 201920239379.X filed on Feb. 25, 2019, and Chinese Patent Application No. 202010110246.X, filed on Feb. 23, 2020, the disclosure of which is incorporated by reference herein in its entirety as part of the present application.

TECHNICAL FIELD

The present disclosure relates to the technical field of bioengineering, and in particular to a biochemical reaction test tube and a use method thereof, and a gene amplification kit.

BACKGROUND

For a conventional small-scale biochemical reaction, one cavity is generally provided in a single test tube to accommodate one kind of solution. When multiple kinds of solutions are required for a reaction, the solutions in different test tubes are drawn out and added to a new test tube. Due to some special reasons such as reagent contamination, a baffle can be provided in a test tube to divide the test tube into two parts, and two solutions A/B are placed in different chambers in the same test tube, such that the two solutions A/B can be mixed to react without opening a cover, which prevents a reagent from leakage and contamination.

Nucleic acid amplification (NAA) such as PCR has the main characteristics of large amplification capacity and extremely-high sensitivity, but easily causes contamination. When a laboratory sample and an amplification target often largely undergo the same conditions, nucleic acid aerosol contamination continues to accumulate in an experimental area, such that the contamination risk continues to increase and the occurrence of false positives will also increase. The high amplification efficiency of PCR technology leads to nucleic acid aerosol contamination, which will cause false positive test results. False positives mean that an experiment is unreliable, which directly cause economic losses for a laboratory. More seriously, if aerosol contamination is formed, the entire PCR laboratory may be contaminated, and even the laboratory needs to be closed.

The contamination of PCR amplification products is the most common contamination. A very small amount of PCR product contamination can cause false positives. Aerosol contamination is the most-likely form of PCR product contamination. Aerosol is a peptized dispersion system formed by small solid and liquid particles with a particle size generally of 0.001 μm to 1,000 μm suspended in a gas medium. Nucleic acid aerosol (namely, DNA/RNA aerosol) refers to nucleic acids dispersed and suspended in a gas medium, which is widely present in places such as laboratory desktops, instruments, consumables, and air. According to calculations, one aerosol particle can include 48,000 copies. A PCR process is accompanied by nucleic acid aerosols, and nucleic acid aerosols will be produced due to rubbing between the air and a liquid surface, centrifugation by a centrifuge, vigorous shaking of a reaction tube, opening of a reaction tube, repeated pipetting of a sample by a pipette, leakage of contaminants, etc.

In addition to the PCR amplification method, the isothermal NAA method has gradually been used in the laboratory. At present, the isothermal NAA method mainly includes the following: loop-mediated isothermal amplification (LAMP), nicking enzyme mediated amplification (NEMA), strand displacement amplification (SDA), rolling circle amplification (RCA), helicase-dependent isothermal DNA amplification (HAD), transcription-based amplification system (TAS), nuclear acid sequence-based amplification (NASBA) (also known as self-sustained sequence replication (3SR), Q-beta replicase-amplified assay, etc. Isothermal amplification gets rid of the limitation of thermal cycling and thus has a greatly-increased application range. Moreover, the currently-used isothermal amplification methods show high sensitivity and specificity, and have an extremely-wide application range in nucleic acid detection. However, high sensitivity will bring about the problems of amplification product contamination and false positives, which will lead to inaccurate determination of a reaction result.

Many reagent manufacturers are working hard to differentiate an NAA product from a nucleic acid derived from a sample and solve the contamination problem from the components of an NAA reagent, and the preventive effect of a UNG enzyme has received increasing attention and affirmation. dU is used instead of dT in PCR products or primers. A dU-substituted PCR product is incubated with UNG, and UDG can cleave an N-glycosidic bond between a uracil base and a sugar-phosphate backbone, such that dU can be removed to prevent the extension of Taq-DNA polymerase, thereby depriving the re-amplification capacity. UNG has no effect on templates without dU. UNG can eliminate uracil from single-stranded or double-stranded DNA, but has no effect on uracil in RNA and single uracil molecules. In an amplification reaction, dUTP is used instead of dTTP, such that a large amount of dU is introduced into a product. Before PCR amplification is conducted once again, a PCR mixture can be treated with UNG to eliminate the residual contamination of a PCR product. Since UNG can be inactivated by the denaturation step in a PCR cycle, UNG will not affect a new PCR product with dU. However, as the enzyme has limited reaction efficiency and there is often a digestion reaction time only of 5 min, UNG generally can only be used to treat the mild PCR product contamination in a PCR mixture, which cannot thoroughly solve the problem.

When primers are synthesized, dU is used instead of dT, such that only the 5' terminus of a PCR product carries dU. After UNG treatment, a primer loses a binding site and cannot be amplified. For the amplification of long fragments (above 1 kb to 2 kb), the efficiency of the dUTP method is lower than that of the dTTP method, and the dU method can overcome this shortcoming. Optimally, dU is designed at the 3' terminus or near the 3' terminus of a dU primer. This method can only be used for the treatment of reagents other than primers.

Current UNG enzyme decontamination methods only pay attention to the enzymolysis of an amplification product before an NAA reaction, and do not consider the direct enzymolysis of an amplification product after an NAA reaction.

SUMMARY OF THE APPLICATION

To overcome the shortcomings in the prior art, the present disclosure provides a biochemical reaction test tube and a use method thereof, and a gene amplification kit.

To achieve the above objective, the present disclosure adopts the following technical solutions.

In a first aspect of the present disclosure, a biochemical reaction test tube is provided, including a tube portion and a cover portion, where the tube portion includes:
- a tube body, where the tube body includes a first chamber and a second chamber, and a bottom of the second chamber is spaced apart from a bottom of the first chamber; and
- a limit unit provided at an outer side of the tube body; and
- when the cover portion seals off the tube portion, a top of the first chamber communicates with a top of the second chamber.

Preferably, a distance between the bottom of the second chamber and the bottom of the first chamber may be at least 3 mm.

Preferably, the second chamber may be provided at an outer side of the first chamber; and/or,
the second chamber may be provided at an inner side of the first chamber.

Preferably, an axis of the second chamber may be collinear with or parallel to an axis of the first chamber.

Preferably, the bottom of the second chamber and a top of the limit unit may be in the same horizontal plane; or,
the bottom of the second chamber may be provided at an upper side of the top of the limit unit.

Preferably, the limit unit may at least partially surround an outer side of the tube body.

Preferably, when the limit unit is subjected to contact conductive heating by a biochemical reaction instrument, the first chamber or the second chamber may contact a heat source of the biochemical reaction instrument.

Preferably, the tube portion may further include:
- a first fitting member provided on a circumferential surface of an inner wall of the tube body; and
the cover portion may include:
- a second fitting member provided on a circumferential surface of an outer wall of the cover portion, where the second fitting member can be connected to the first fitting member, such that the cover portion seals off the tube portion.

Preferably, there may be a plurality of first fitting members, and the plurality of first fitting members may be arranged along an axial direction of the tube portion;
there may be a plurality of second fitting members, and the plurality of second fitting members may be arranged along an axial direction of the cover portion; and
a second fitting member at the lowermost side of the cover portion may be at least connected to a first fitting member at the uppermost side of the tube portion.

Preferably, the biochemical reaction test tube may further include:
- a connecting member; and both ends of the connecting member may be connected to the tube portion and the cover portion, respectively.

Preferably, the cover portion may include:
- an auxiliary member provided on the outer wall of the cover portion; and
- when the cover portion seals off the tube portion, the auxiliary member protrudes from the tube portion.

Preferably, a thickness of the auxiliary member may be smaller than a thickness of a top of the cover portion; or
the auxiliary member may have a thickness smaller than or equal to 0.4 mm.

Preferably, the cover portion may include:
- a hollow member, which is provided inside the cover portion in a penetrating manner and includes:
  - a first opening element provided at an upper end of the hollow member; and
  - a second opening element provided at a lower end of the hollow member; and
- a sealing member, which is configured to seal off the hollow member and includes:
  - a first sealing element configured to seal off the first opening element; and
  - a second sealing element configured to seal off the second opening element.

Preferably, when the sealing member seals off the hollow member, the first sealing element may not contact the second sealing element; or
the first sealing element may destroy the second sealing element.

Preferably, the hollow member may include:
- a third fitting member provided on a circumferential surface of an inner wall of the hollow member; and
the sealing member may include:
- a fourth fitting member provided on a circumferential surface of an outer wall of the first sealing element, where the third fitting member can be connected to the fourth fitting member, such that the first sealing element seals off the first opening element.

Preferably, the bottom of the first chamber may have a cylindrical structure or a conical structure.

Preferably, a top of the cylindrical structure or the conical structure may have an inner diameter of 1.5 mm to 8 mm.

Preferably, the top of the second chamber may have an inner diameter of 5 mm to 15 mm.

Preferably, the biochemical reaction test tube may further include:
- a metal warm-bath instrument configured to subject a biochemical reaction solution in the biochemical reaction test tube to contact conductive heating.

Preferably, the biochemical reaction test tube may further include:
- a biochemical reaction optical detection instrument configured to acquire an optical signal of the biochemical reaction solution in the biochemical reaction test tube when the biochemical reaction test tube is subjected to contact conductive heating.

In a second aspect of the present disclosure, a gene amplification kit is provided, including:
- the biochemical reaction test tube described above;
- an NAA reagent; and
- a functional reaction reagent;
where one of the NAA reagent and the functional reaction reagent is placed inside the first chamber, and the other one of the NAA reagent and the functional reaction reagent is placed inside the second chamber; and
in the case where the cover portion seals off the tube portion:
when the cover portion seals off the tube portion:
after the NAA reagent contacts the heat source to complete an amplification reaction, the reactivity of the functional reaction reagent remains excellent; and
after the biochemical reaction test tube is vertically flipped at 180°, the functional reaction reagent is mixed with an amplification product obtained after the amplification reaction is completed.

Preferably, the NAA reagent may include dUTP, and the functional reaction reagent may be a UNG enzyme-containing solution;

the NAA reagent may include an NAA primer with a sequence targeted by an endonuclease, and the functional reaction reagent may be an endonuclease-containing solution; or the NAA reagent may include an NAA primer, and the functional reaction reagent may be a nuclease-containing solution.

In a third aspect of the present disclosure, a use method of the biochemical reaction test tube is provided, including:

placing one of an NAA reagent and a functional reaction reagent inside the first chamber, and placing the other one of the NAA reagent and the functional reaction reagent inside the second chamber;

inserting the biochemical reaction test tube into an amplification instrument for temperature control, and only subjecting the first chamber or the second chamber holding the NAA reagent to contact conductive heating; and after an NAA reaction is completed, mixing the functional reaction reagent with an amplification product obtained after the amplification reaction is completed.

Preferably, after the NAA reaction is completed, the biochemical reaction test tube may be removed from the amplification instrument and then vertically flipped at 180° such that the biochemical reaction test tube is in an inverted state and the functional reaction reagent is mixed with an amplification product obtained after the amplification reaction is completed.

Preferably, the functional reaction reagent may be a lyase, and the functional reaction reagent may be mixed with the amplification product obtained after the amplification reaction is completed to lyse the amplification product.

Preferably, the amplification instrument may include a PCR instrument and a fluorescence detection instrument.

Compared with the prior art, the above technical solutions adopted by the present disclosure have the following technical effects:

In the biochemical reaction test tube of the present disclosure, a first chamber and a second chamber are provided at different heights and used to hold different reaction components and solutions. In actual use, only one of the first chamber and the second chamber is heated to complete a biochemical reaction and a relevant biochemical reaction signal such as a fluorescence signal is acquired. When the test tube is vertically flipped at 180° and shaken, the solutions in the first chamber and the second chamber are mixed to further achieve a reaction, which eliminates harmful results. For example, a nucleic acid-degrading enzyme solution and an NAA product solution in different chambers are mixed to degrade an amplification product, which prevents the amplification product solution from leaking and polluting an operating environment.

REFERENCE NUMERALS tube portion: 10; tube body: 11; limit unit: 12; first chamber: 13; second chamber: 14; first fitting member: 15; cover portion: 20; second fitting member: 21; connecting member: 30; auxiliary member: 40; hollow member: 50; first opening element: 51; second opening element: 52; third fitting member: 53; sealing member: 60; first sealing element: 61; second sealing element: 62; fourth fitting member: 63; limiting part: 611; destroying part: 612; metal warm-bath instrument: 70; and biochemical reaction optical detection instrument: 80.

DETAILED DESCRIPTION

The technical solutions in the examples of the present disclosure are clearly and completely described below with reference to the accompanying drawings in the examples of the present disclosure. Apparently, the described examples are merely a part rather than all of the examples of the present disclosure. All other examples obtained by a person of ordinary skill in the art based on the examples of the present disclosure without creative efforts shall fall within the protection scope of the present disclosure.

It should be noted that the examples in the present disclosure or features in the examples may be combined in a non-conflicting manner.

The present disclosure is further described below with reference to the accompanying drawings and specific examples, but the present disclosure is not limited thereto.

Example 1

Figure 1:
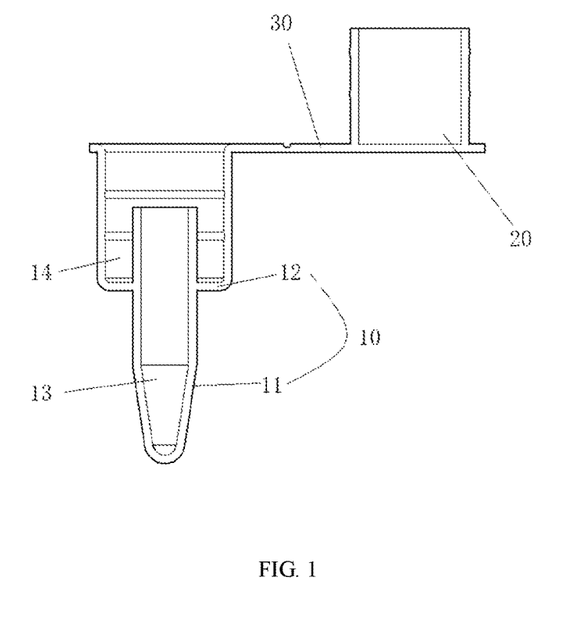
FIG. 1 is a schematic cross-sectional view of a biochemical reaction test tube according to an exemplary example of the present disclosure (the tube portion is not sealed off by the cover portion).
Figure 2:
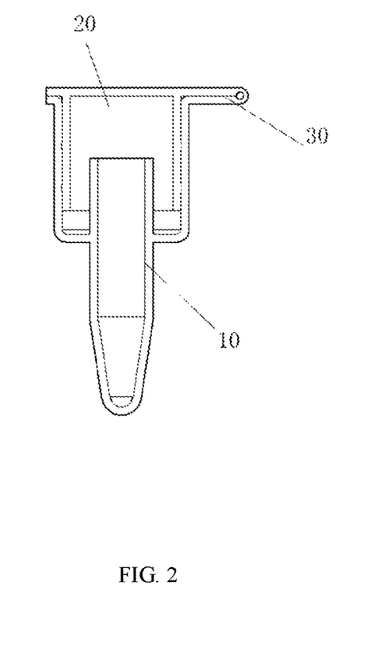
FIG. 2 is a schematic cross-sectional view of a biochemical reaction test tube according to an exemplary example of the present disclosure (the tube portion is sealed off by the cover portion).

According to an exemplary example of the present disclosure, as shown in FIG. 1 and FIG. 2, a biochemical reaction test tube includes a tube portion 10 and a cover portion 20, and the tube portion 10 includes a tube body 11 and a limit unit 12. The limit unit 12 is provided on an outer wall of the tube body 11, and the tube body 11 includes a first chamber 13 and a second chamber 14. When the cover portion 20 seals off the tube portion 10, a top of the first chamber 13 communicates with a top of the second chamber 14.

The first chamber 13 is provided to hold an NAA reagent, and the second chamber 14 is provided to hold a functional reaction reagent for degrading an amplification product in the first chamber 13; or, the second chamber 14 is provided to hold an NAA reagent, and the first chamber 13 is provided to hold a functional reaction reagent for degrading an amplification product in the second chamber 14. After an NAA reaction is completed, the biochemical reaction test tube is vertically flipped at 180°, such that the functional reaction reagent is mixed with an amplification product to degrade the amplification product.

The functional reaction reagent includes, but is not limited to, a degrading enzyme, a lysis solution, a probe, a buffer, a diluent, and the like, or reagents for subsequent reactions after an amplification reaction is completed.

A bottom of the second chamber 14 may be spaced apart from a bottom of the first chamber 13, that is, a distance between the bottom of the second chamber 14 and the horizontal plane may be greater than a distance between the bottom of the first chamber 13 and the horizontal plane.

A distance between the bottom of the second chamber 14 and the bottom of the first chamber 13 may be at least 3 mm.

The second chamber 14 may be provided at an outer side of the first chamber 13; the second chamber 14 may be provided between an inner wall of the tube body 11 and an outer wall of the first chamber 13; and the second chamber 14 may be an annular chamber, that is, the second chamber 14 surrounds a circumferential surface of the outer wall of the first chamber 13. In this case, an axis of the second chamber 14 is collinear with an axis of the first chamber 13.

Correspondingly, the second chamber 14 may be provided at an inner side of the first chamber 13; and the second chamber 14 may be an annular chamber, that is, the second chamber 14 surrounds a circumferential surface of an inner wall of the first chamber 13. In this case, the axis of the second chamber 14 is collinear with the axis of the first chamber 13.

In another implementation of this example, the second chamber 14 is provided at an outer side of the first chamber 13; the second chamber 14 is provided between the inner wall of the tube body 11 and the outer wall of the first chamber 13; and the second chamber 14 may be a circular chamber, that is, a circumferential surface of an outer wall of the second chamber 14 is tangential to a circumferential surface of the outer wall of the first chamber 13. In this case, the axis of the second chamber 14 is parallel to the axis of the first chamber 13. There may be a plurality of second chambers 14, and the plurality of second chambers 14 are surroundingly provided on a circumferential surface of the outer wall of the first chamber 13 with the first chamber 13 as a center.

Correspondingly, the second chamber 14 may be provided at an inner side of the first chamber 13; and the second chamber 14 is a circular chamber, that is, a circumferential surface of the outer wall of the second chamber 14 is tangential to a circumferential surface of the inner wall of the first chamber 13. In this case, the axis of the second chamber 14 is parallel to the axis of the first chamber 13. There may be a plurality of second chambers 14, and the plurality of second chambers 14 are surroundingly provided on a circumferential surface of the inner wall of the first chamber 13 with the first chamber 13 as a center.

In the above structure, the second chamber 14 and the first chamber 13 may be provided integrally or separately. In the case where the second chamber 14 and the first chamber 13 are provided separately, the second chamber 14 is removably provided at an outer side of the first chamber 13, and a removable manner includes, but is not limited to, a snap connection.

The limit unit 12 at least partially surrounds the tube body 11, that is, a connecting side of the limit unit 12 with the tube body 11 is in an arc shape with at least an acute central angle. Specifically, the limit unit 12 may be a full skirt, a half skirt, or a quarter skirt.

A distance between a top of the limit unit 12 and a bottom of the second chamber 14 may be 0, that is, the top of the limit unit 12 and the bottom of the second chamber 14 are in the same horizontal plane; or, a distance between the top of the limit unit 12 and the bottom of the second chamber 14 may be greater than 0, that is, in a vertical direction, the limit unit 12 is provided at a lower side of the second chamber 14.

The limit unit 12 may be a symmetrical cylinder or cone, which can be inserted into a biochemical reaction instrument at any angle for fixing. For example, the limit unit 12 can be inserted into a heating base of a PCR amplification instrument at any angle for fixing, and can subject a biochemical reaction result of a solution in the first chamber 13 to optical signal acquisition and detection from a bottom surface of the first chamber 13 or a side surface adjacent to the bottom surface.

Or, the limit unit 12 is an asymmetrical cylinder, which can only be inserted into a biochemical reaction instrument at a single angle for fixing, and can only subject a biochemical reaction result of a solution in the first chamber 13 to optical signal acquisition and detection from a single direction.

When the limit unit 12 is subjected to contact conductive heating by a biochemical reaction instrument, a solution (with an NAA reagent) at the bottom of the first chamber 13 is subjected to contact conductive heating, while a solution (with a functional reaction reagent) at the bottom of the second chamber 14 is not subjected to contact conductive heating; or, a solution (with an NAA reagent) at the bottom of the second chamber 14 is subjected to contact conductive heating, while a solution (with a functional reaction reagent) at the bottom of the first chamber 13 is not subjected to contact conductive heating.

Figure 3:
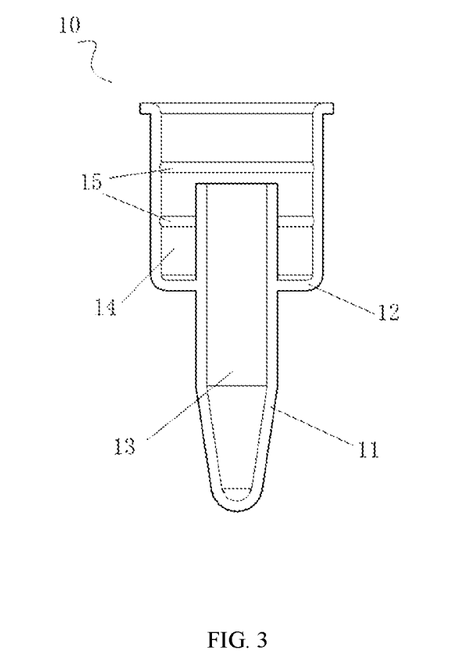
FIG. 3 is a schematic cross-sectional view of a tube portion of a biochemical reaction test tube according to an exemplary example of the present disclosure.

As shown in FIG. 1 to FIG. 3, the bottom of the first chamber 13 may have a cylindrical structure or a conical structure, which can match an inner hole of a heating base of a biochemical reaction instrument.

A top of the cylindrical or conical structure of the first chamber 13 may have an inner diameter of 1.5 mm to 8 mm, and the top of the second chamber 14 may have an inner diameter of 5 mm to 15 mm.

Figure 4:
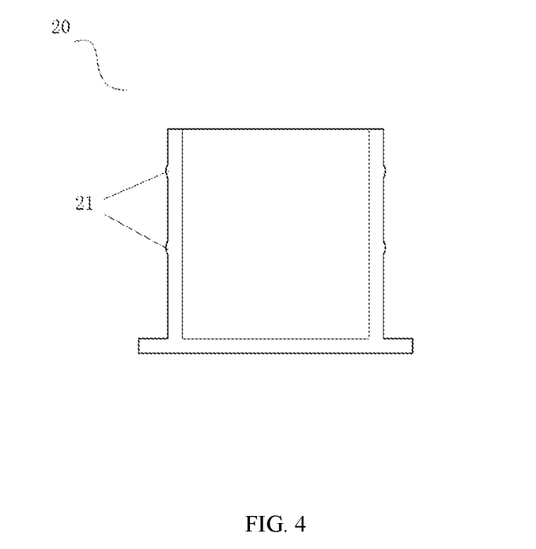
FIG. 4 is a schematic cross-sectional view of a cover portion of a biochemical reaction test tube according to an exemplary example of the present disclosure.

In order to improve the sealing effect between the tube portion 10 and the cover portion 20, the tube portion 10 and the cover portion 20 are provided with a first fitting member 15 and a second fitting member 21, respectively.

As shown in FIG. 3, the first fitting member 15 is provided on a circumferential surface of the inner wall of the tube body 11, and there may be at least one first fitting member 15.

As shown in FIG. 4, the second fitting member 21 is provided on a circumferential surface of the outer wall of the cover portion 20, and there may be at least one second fitting member 21.

When the cover portion 20 seals off the tube portion 10, the second fitting member 21 is connected to the first fitting member 15, such that the cover portion 20 and the tube portion 10 fit with each other to improve the sealing effect of the cover portion 20 for the tube portion 10.

The first fitting member 15 is a groove (or a sealing groove), and the second fitting member 21 is a protrusion (or a raised sealing ring); or the first fitting member 15 is a protrusion (or a raised sealing ring), and the second fitting member 21 is a groove (or a sealing groove).

There may be a plurality of first fitting members 15, and the first fitting members 15 are arranged along an axial direction of the tube portion 10. Similarly, there may be a plurality of second fitting members 21, and the second fitting members 21 are arranged along an axial direction of the cover portion 20.

The first fitting members 15 and the second fitting members 21 may be connected in a one-to-one correspondence. Specifically, when the cover portion 20 seals off the tube portion 10, a first fitting member 15 at the lowermost side of the tube portion 10 is connected to a second fitting member 21 at the lowermost side of the cover portion 20; and a first fitting member 15 at the uppermost side of the tube portion 10 is connected to a second fitting member 21 at the uppermost side of the cover portion 20. In this case, a relatively-large external force is required to remove the cover portion 20 to expose an inner chamber of the tube portion 10.

The first fitting members 15 and the second fitting members 21 may not be connected in a one-to-one correspondence. For example, when the cover portion 20 seals off the tube portion 10, a first fitting member 15 at the uppermost side of the tube portion 10 is connected to a second fitting member 21 at the lowermost side of the cover portion 20. In this case, the cover portion 20 can be easily removed to expose an inner chamber of the tube portion 10.

It can be known from the above that, in order to allow the cover portion 20 to seal off the tube portion 10, the first fitting member 15 at the uppermost side of the tube portion 10 is at least connected to the second fitting member 21 at the lowermost side of the cover portion 20.

In order to ensure a one-to-one correspondence between the tube portion 10 and the cover portion 20, a connecting member 30 is also provided to connect the tube portion 10 and the cover portion 20. Specifically, a first end of the connecting member 30 is connected to an outer wall of a top of the tube portion 10, and a second end of the connecting member 30 is connected to an outer wall of a top of the cover portion 20.

The connecting member 30 may be a connecting stranded strip.

As shown in FIG. 2, when the cover portion 20 seals off the tube portion 10, except for the folded connecting member 30, an outer edge of a top of the cover portion 20 does not extend beyond any part of a top edge of the tube portion 10.

Example 2

In this example, a specific implementation of the present disclosure is provided, which is an improved implementation for Example 1 and can facilitate the removal of the cover portion 20.

Figure 5:
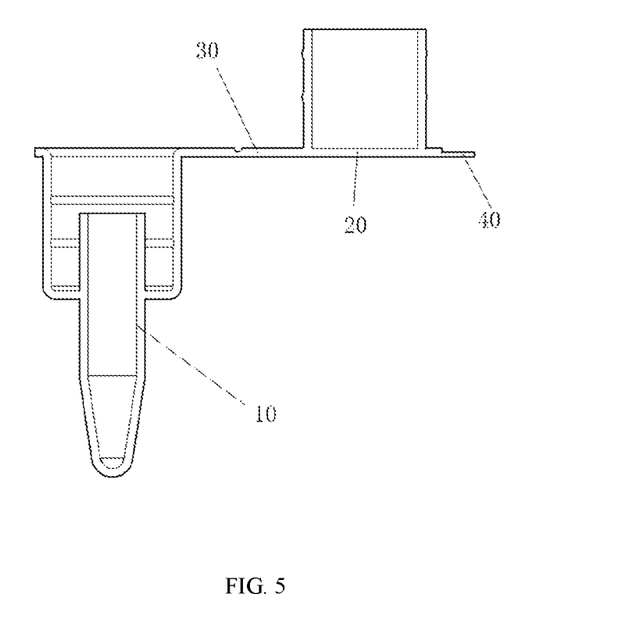
FIG. 5 is a schematic cross-sectional view of a biochemical reaction test tube according to a specific implementation of the present disclosure (the tube portion is not sealed off by the cover portion).
Figure 6:
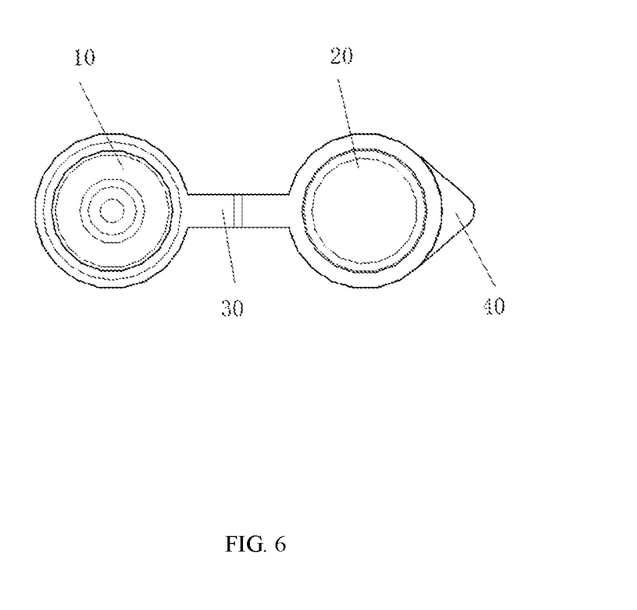
FIG. 6 is a schematic top view of a biochemical reaction test tube according to a specific implementation of the present disclosure.

As shown in FIG. 5 and FIG. 6, a biochemical reaction test tube includes a tube portion 10, a cover portion 20, a connecting member 30, and an auxiliary member 40. Structures of and a connection relationship among the tube portion 10, the cover portion 20, and the connecting member 30 are basically the same as that in Example 1, which will not be repeated here.

The auxiliary member 40 is provided on an outer wall of the cover portion 20; and when the cover portion 20 seals off the tube portion 10, the auxiliary member 40 protrudes from the tube portion 10. That is, the auxiliary member 40 is a protrusion that extends out from a top edge of the tube portion 10 along an outer edge of a top of the cover portion 20 at a specified length.

The auxiliary member 40 is provided at a symmetrical side relative to the connecting member 30.

A thickness of the auxiliary member 40 is smaller than a thickness of the top of the cover portion 20.

The auxiliary member 40 may have a thickness smaller than or equal to 0.04 mm.

Example 3

In this example, a specific implementation of the present disclosure is provided, which is an improved implementation for Example 1 and can facilitate the addition of a solution into the second chamber 14.

Figure 7:
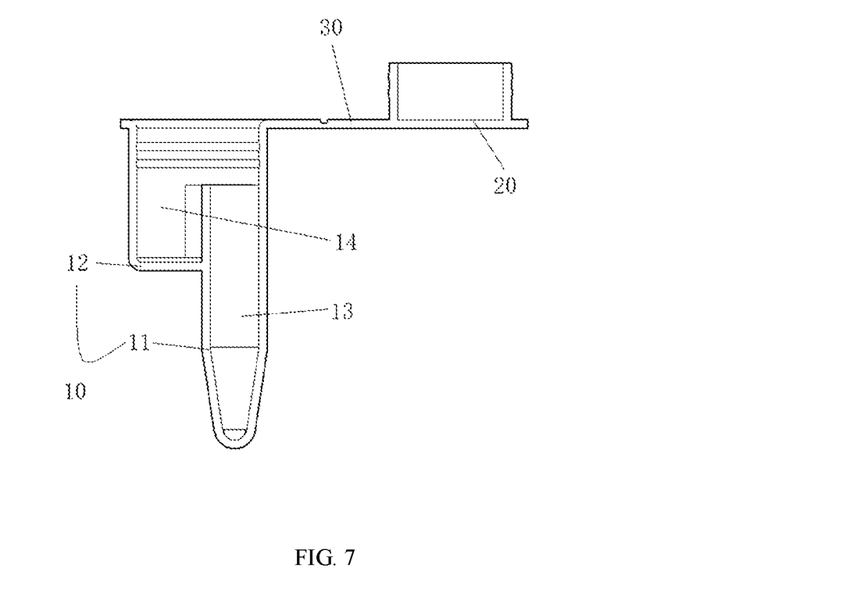
FIG. 7 is a schematic cross-sectional view of a biochemical reaction test tube according to a specific implementation of the present disclosure (the tube portion is not sealed off by the cover portion).
Figure 8:
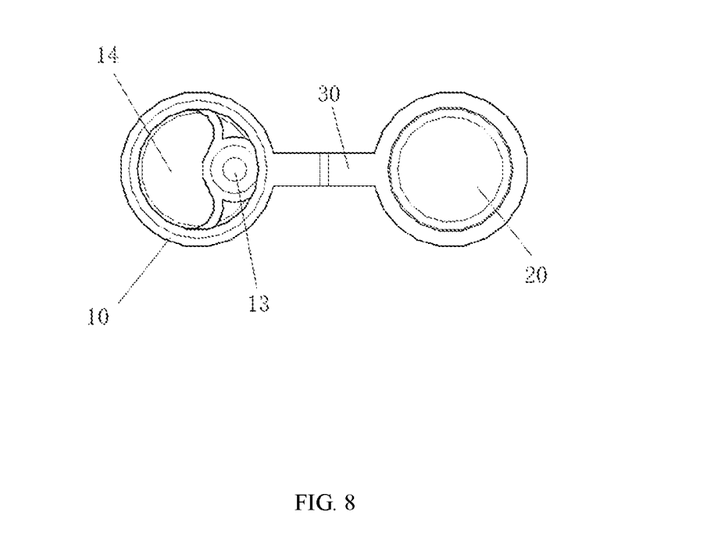
FIG. 8 is a schematic top view of a biochemical reaction test tube according to a specific implementation of the present disclosure.

As shown in FIG. 7 and FIG. 8, a biochemical reaction test tube includes a tube portion 10, a cover portion 20, and a connecting member 30. Structures of and a connection relationship between the cover portion 20 and the connecting member 30 are basically the same as that in Example 1, which will not be repeated here.

As shown in FIG. 7 and FIG. 8, in the tube portion 10, the bottom of the first chamber 13 may have a cylindrical structure or a conical structure, which can match an inner hole of a biochemical reaction instrument; the second chamber 14 is provided between the outer wall of the tube body 11 and the inner wall of the limit unit 12; and an axis of the second chamber 14 is parallel to an axis of the first chamber 13, that is, the first chamber 13 is provided at an eccentric position of a bottom surface of the second chamber 14.

Specifically, an outer wall of the first chamber 13 at one side is far away from an inner wall of the limit unit 12 at a corresponding side, and an outer wall of the first chamber 13 at the other side is close to an inner wall of the limit unit 12 at a corresponding side, which makes a radial size of the second chamber 14 increase. Therefore, a tip of a pipette tip can be inserted deeply into the second chamber 14, which allows a solution to enter the second chamber 14 smoothly and prevents the solution from entering the first chamber 13 due to an improper operation of an operator.

Example 4

In this example, a specific implementation of the present disclosure is provided, which is an improved implementation for Example 1 and can further reduce the probability of contamination to the biochemical reaction test tube.

Figure 9:
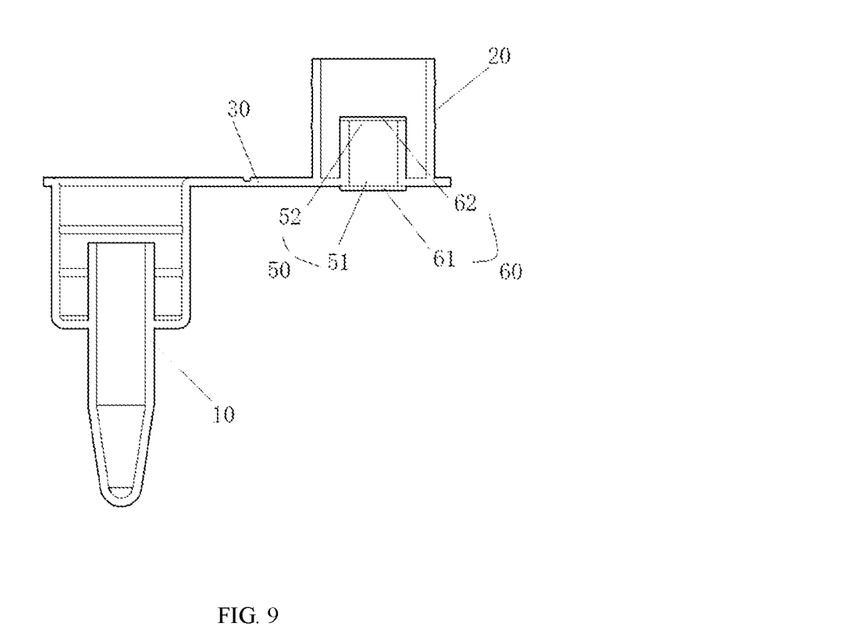
FIG. 9 is a schematic cross-sectional view of a biochemical reaction test tube according to a specific implementation of the present disclosure (the tube portion is not sealed off by the cover portion).
Figure 10:
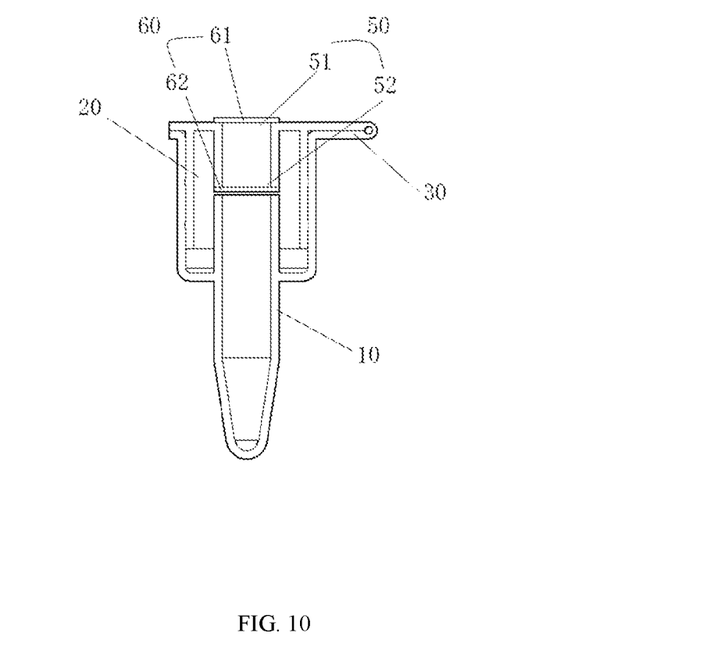
FIG. 10 is a schematic cross-sectional view of a biochemical reaction test tube according to a specific implementation of the present disclosure (the tube portion is sealed off by the cover portion).

As shown in FIG. 9 and FIG. 10, a biochemical reaction test tube includes a tube portion 10, a cover portion 20, and a connecting member 30. Structures of and a connection relationship between the tube portion 10 and the connecting member 30 are basically the same as that in Example 1, which will not be repeated here.

As shown in FIG. 9 and FIG. 10, on the basis of Example 1, the cover portion 20 further includes a hollow member 50 and a sealing member 60, where the hollow member 50 is provided inside the cover portion 20 in a penetrating manner and the sealing member 60 seals off the hollow member 50.

The hollow member 50 includes a first opening element 51 provided at an upper end of the hollow member 50, such that a solution enters an interior of the hollow member 50 from an outer side of the cover portion 20 through the first opening element 51.

Correspondingly, the sealing member 60 includes a first sealing element 61, which seals off the first opening element 51.

Specifically, the first sealing element 61 is a sealing film or a sealing film with a sticker. During operation, the first sealing element 61 is removed, a biochemical reaction solution is added into the hollow member 50, and then the first sealing element 61 is used to seal off the first opening element 51.

On the basis of the above structure, in order to further improve the operation efficiency, the hollow member 50 further includes a second opening element 52 provided at a lower end of the hollow member 50, and the sealing member 60 further includes a second sealing element 62 configured to seal off the second opening element 62.

Specifically, the second sealing element 62 is an easily-destroyed sealing element, such as a sealing film, an aluminum foil with a sealing and pasting material, or other film materials. In the first operation, the first sealing element 61 is removed, a biochemical reaction solution is added into the hollow member 50, and then the first sealing element 61 is used to seal off the first opening element 51; and in the second operation, the first sealing element 61 is removed, and a tool is used by an operator to sequentially pass through the first opening element 51 and the second opening element 52 and then destroy the second sealing element 62, such that the biochemical reaction solution inside the hollow member 50 enters an interior of the tube body 11, and finally the first sealing element 61 is used to seal off the first opening element 51.

Example 5

In this example, a specific implementation of the present disclosure is provided, which is an improved implementation for Example 1 and can further reduce the probability of contamination to the biochemical reaction test tube.

Figure 11:
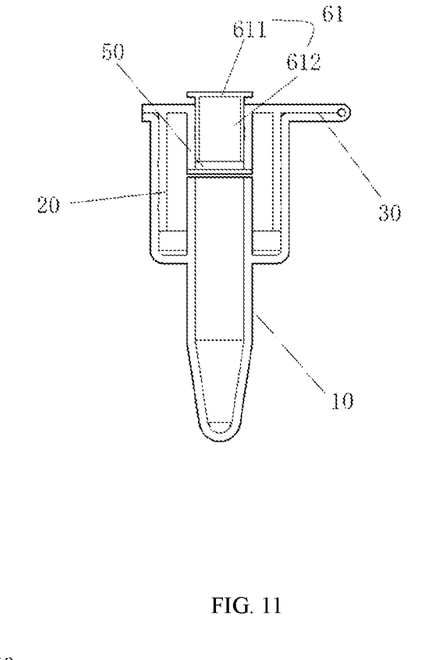
FIG. 11 is a schematic cross-sectional view of a biochemical reaction test tube according to a specific implementation of the present disclosure (the tube portion is sealed off by the cover portion).

As shown in FIG. 11, a biochemical reaction test tube includes a tube portion 10, a cover portion 20, and a connecting member 30. Structures of and a connection relationship between the tube portion 10 and the connecting member 30 are basically the same as that in Example 1, which will not be repeated here.

As shown in FIG. 11, on the basis of Example 1, the cover portion 20 further includes a hollow member 50 and a sealing member 60, where the hollow member 50 is provided inside the cover portion 20 in a penetrating manner and the sealing member 60 seals off the hollow member 50.

The hollow member 50 includes a first opening element 51 provided at an upper end of the hollow member 50 and a second opening element 52 provided at a lower end of the hollow member 50.

Correspondingly, the sealing member 60 includes a first sealing element 61 to seal off the first opening element 51 and a second sealing element 62 to seal off the second opening element 52, and when the first sealing element 61 completely seals off the first opening element 51, the first sealing element 61 destroys the second sealing element 62.

The first sealing element 61 includes a limiting part 611 and a destroying part 612, and the destroying part 612 is provided at a lower end of the limiting part 611. An inner diameter of the limiting part 611 is greater than an inner diameter of the hollow member 50, and an inner diameter of the destroying part 612 is less than or equal to an inner diameter of the hollow member 50. When the first sealing element 61 completely seals off the first opening element 51, a bottom end of the destroying part 612 destroys the second sealing element 62.

Specifically, the limiting part 611 is a cover plate, and the destroying part 612 is a hollow tube.

The limiting part 611 and the destroying part 612 are movably connected, that is, when a specified operation (such as opening) is applied to the limiting part 611, a biochemical reaction component or solution can be added to the destroying part 612.

Specifically, the limiting part 611 and the destroying part 612 may be in nested connection, threaded connection, snap connection, etc., for example, the limiting part 611 and the destroying part 612 are connected in the same manner as that between the cover portion 20 and the tube portion 10.

Specifically, the second sealing element 62 is an easily-destroyed sealing element, such as a sealing film, an aluminum foil with a sealing and pasting material, or other film materials.

Figure 12:
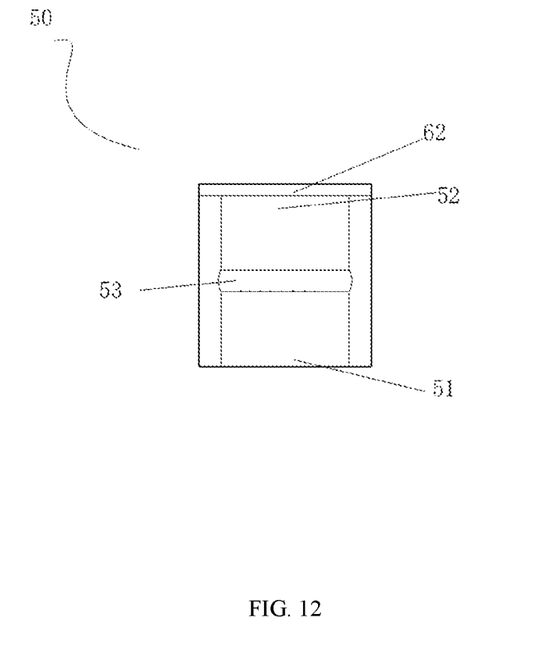
FIG. 12 is a schematic cross-sectional view of a hollow member of a biochemical reaction test tube according to a specific implementation of the present disclosure.
Figure 13:
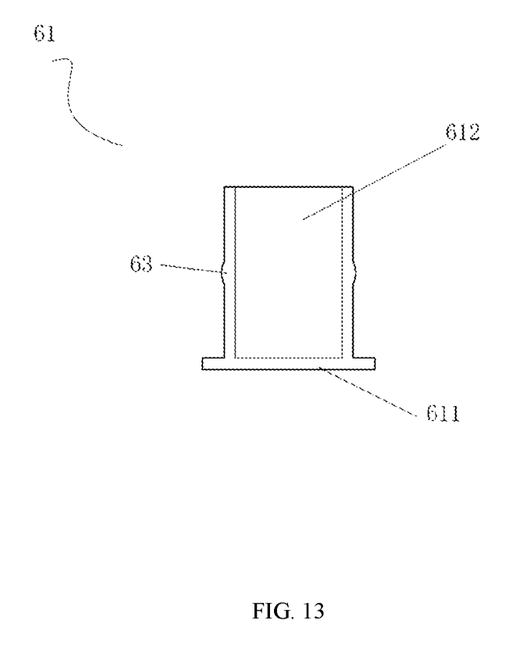
FIG. 13 is a schematic cross-sectional view of a first sealing element of a biochemical reaction test tube according to a specific implementation of the present disclosure.

In order to improve the sealing effect between the hollow member 50 and the sealing member 60, the hollow member 50 and the sealing member 60 are provided with a third fitting member 53 and a fourth fitting member 63, respectively.

As shown in FIG. 12, the third fitting member 53 is provided on a circumferential surface of an inner wall of the hollow member 50, and there may be at least one third fitting member 53.

As shown in FIG. 13, the fourth fitting member 63 is provided on a circumferential surface of an outer wall of the first sealing element 61, and there may be at least one fourth fitting member 63.

When the first sealing element 61 seals off the first opening element 51, the fourth fitting member 63 is connected to the third fitting member 53, such that the first sealing element 61 and the hollow member 50 fit with each other to improve the sealing effect of the first sealing element 61 for the first opening element 51.

The third fitting member 53 is a groove (or a sealing groove), and the fourth fitting member 63 is a protrusion (or a raised sealing ring); or the third fitting member 53 is a protrusion (or a raised sealing ring), and the fourth fitting member 63 is a groove (or a sealing groove).

There may be a plurality of third fitting members 53, and the third fitting members 53 are arranged along an axial direction of the hollow member 50. Similarly, there may be a plurality of fourth fitting members 63, and the fourth fitting members 63 are arranged along an axial direction of the first sealing element 61.

The third fitting members 53 and the fourth fitting members 63 may be connected in a one-to-one correspondence. Specifically, a third fitting member 53 at the lowermost side of the hollow member 50 is connected to a fourth fitting member 63 at the lowermost side of the first sealing element 61; and the third fitting member 53 at the uppermost side of the hollow member 50 is connected to a fourth fitting member 63 at the uppermost side of the first sealing element 61. In this case, the first sealing element 61 destroys the second sealing element 62.

The third fitting members 53 and the fourth fitting members 63 may not be connected in a one-to-one correspondence. For example, a third fitting member 53 at the uppermost side of the hollow member 50 is connected to a fourth fitting member 63 at the lowermost side of the first sealing element 61. In this case, the first sealing element 61 does not destroy the second sealing element 62.

When the biochemical reaction test tube of this example is used, the limiting part 611 of the first sealing element 61 can be opened, and a biochemical reaction component or solution can be placed inside the destroying part 612; the first sealing element 61 is inserted into the hollow member 50 through the first opening element 51 and destroys the second sealing element 62; and the biochemical reaction component or solution in the destroying part 612 is mixed with a solution inside the tube body 11 to further achieve a biochemical reaction. For example, a nucleic acid-degrading enzyme is placed in the destroying part 612 to degrade an NAA product inside the biochemical reaction test tube.

Example 6

In this example, a specific implementation of the present disclosure is provided, which is an extended implementation for Examples 1 to 5.

Figure 14:
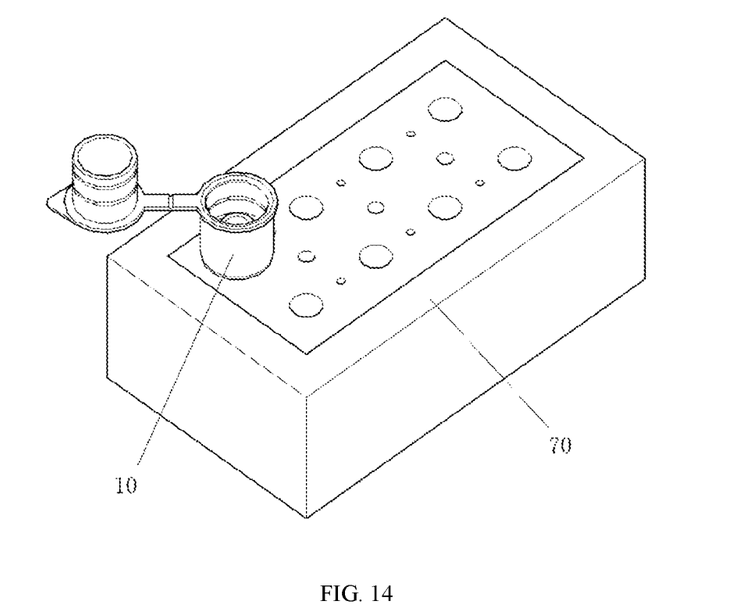
FIG. 14 is schematic diagram of a biochemical reaction test tube with a metal warm-bath instrument according to a specific implementation of the present disclosure.

As shown in FIG. 14, the biochemical reaction test tube also includes a metal warm-bath instrument 70 that achieves contact temperature conduction control for a solution inside the biochemical reaction test tube, where a specified temperature value can be set, such that a temperature can be stably kept at a specified value according to set conditions or can cyclically change among multiple temperature values.

Figure 15:
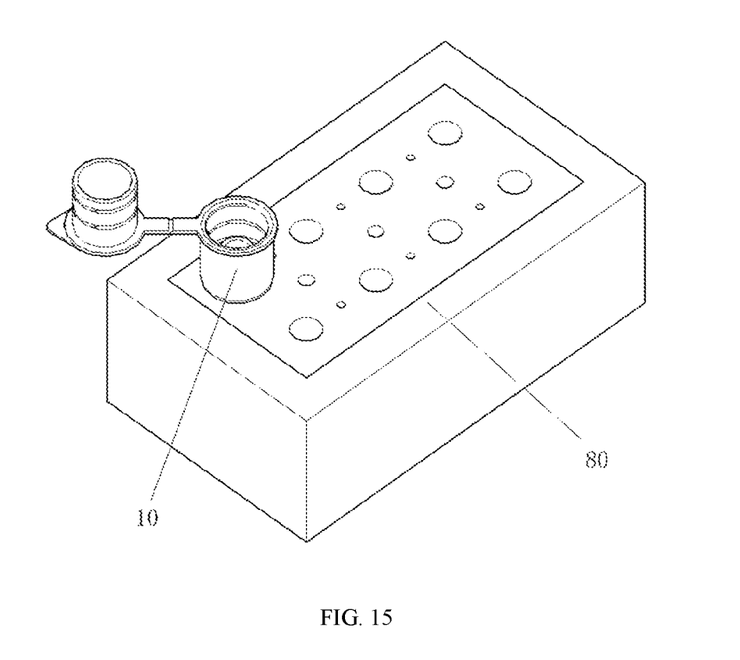
FIG. 15 is schematic diagram of a biochemical reaction test tube with a biochemical reaction optical detection instrument according to a specific implementation of the present disclosure.

As shown in FIG. 15, the biochemical reaction test tube also includes a biochemical reaction optical detection instrument 80 that subjects a solution inside the biochemical reaction test tube to contact temperature conduction control. The biochemical reaction optical detection instrument 80 acquires an optical signal of the biochemical reaction solution inside the biochemical reaction test tube during the temperature conduction to the solution inside the biochemical reaction test tube.

Example 7

In this example, the use of the biochemical reaction test tube of Examples 1 to 5 are provided.

A gene amplification kit is provided, which at least includes a biochemical reaction test tube, an NAA reagent, and a functional reaction reagent. The NAA reagent is placed in the first chamber 13 of the tube body 11 and the functional reaction reagent is placed in the second chamber 14 of the tube body 11; or, the NAA reagent is placed in the second chamber 14 of the tube body 11 and the functional reaction reagent is placed in the first chamber 13 of the tube body 11.

The thermal sensitivity of the functional reaction reagent is different from that of the NAA reagent.

Specifically, the functional reaction reagent includes, but is not limited to, a degrading enzyme, a lysis solution, a probe, a buffer, a diluent, and the like, or reagents for subsequent reactions after an amplification reaction is completed.

In a first specific implementation of this example, the NAA reagent is a dUTP-containing NAA reagent, and the functional reaction reagent is a UNG enzyme-containing solution. In this implementation, the dUTP-containing NAA reagent is used such that an NAA reaction is completed at a controlled temperature and a specified amount of dU is introduced into an amplification product. Specifically, after the NAA reagent in the first chamber 13 (or the second chamber 14) is heated to complete an amplification reaction, the reactivity of the UNG enzyme in the second chamber 14 (or the first chamber 13) remains excellent; and the biochemical reaction test tube is vertically flipped at 180° and shaken, such that a pre-added UNG enzyme solution in the second chamber 14 (or the first chamber 13) or a solution of a UNG enzyme that is pre-added, dissolved, and solidified in the second chamber 14 (or the first chamber 13) is mixed with an amplification product solution in the first chamber 13 (or the second chamber 14) to enzymatically degrade a nucleic acid product introduced with dU.

In a second specific implementation of this example, the NAA reagent is an NAA primer with a sequence targeted by an endonuclease and an amplification reagent thereof, and the functional reaction reagent is an endonuclease-containing solution. In this implementation, the NAA primer with a sequence targeted by an endonuclease and an amplification reagent thereof are used to achieve the amplification of a nucleic acid product introduced with a sequence targeted by an endonuclease at a controlled temperature. Specifically, after the NAA reagent in the first chamber 13 (or the second chamber 14) is heated to complete an amplification reaction, the biochemical reaction test tube is vertically flipped at 180° and shaken, such that a pre-added endonuclease solution in the second chamber 14 (or the first chamber 13) or a solution of an endonuclease that is pre-added, dissolved, and solidified in the second chamber 14 (or the first chamber 13) is mixed with an amplification product solution in the first chamber 13 (or the second chamber 14) to enzymatically degrade a nucleic acid product.

In a third specific implementation of this example, the NAA reagent is an NAA primer and an amplification reagent thereof, and the functional reaction reagent is a nuclease-containing solution. In this implementation, the NAA primer and the amplification reagent thereof are used to complete the amplification of a product at a controlled temperature. Specifically, after the NAA reagent in the first chamber 13 (or the second chamber 14) is heated to complete an amplification reaction, the biochemical reaction test tube is vertically flipped at 180° and shaken, such that a pre-added nuclease solution in the second chamber 14 (or the first chamber 13) or a solution of a nuclease that is pre-added, dissolved, and solidified in the second chamber 14 (or the first chamber 13) is mixed with an amplification product solution in the first chamber 13 (or the second chamber 14) to enzymatically degrade a nucleic acid product.

Example 8

In this example, a use method of the biochemical reaction test tube of Examples 1 to 5 are provided.

The use method of the biochemical reaction test tube includes:
- one of the NAA reagent and the functional reaction reagent is placed inside the first chamber 13, and the other one of the NAA reagent and the functional reaction reagent is placed inside the second chamber 14;
- the biochemical reaction test tube is inserted into an amplification instrument for temperature control, and only the first chamber 13 or the second chamber 14 holding the NAA reagent is subjected to contact conductive heating; and
- after an NAA reaction is completed, the functional reaction reagent is mixed with an amplification product obtained after the amplification reaction is completed.

Specifically, after the NAA reaction is completed, the biochemical reaction test tube is removed from the amplification instrument and then vertically flipped at 180° such that the biochemical reaction test tube is in an inverted state and the functional reaction reagent is mixed with an amplification product obtained after the amplification reaction is completed.

As a first specific implementation of this example, the use method includes:
- a PCR amplification reagent is placed in the first chamber 13 and an enzyme solution for cleaving a PCR amplification product is placed in the second chamber 14;
- the biochemical reaction test tube is inserted into an NAA PCR instrument for temperature control, at which time, only the solution in the first chamber 13 is subjected to temperature conduction, and the second chamber 14 does not contact with a heat transfer component of the PCR instrument;
- when the NAA reaction is completed, the biochemical reaction test tube is pulled out and placed upside down, such that the solutions in the first chamber 13 and the second chamber 14 are mixed; and
- the biochemical reaction test tube is placed upside down in an environment suitable for the degradation of the enzyme, and incubated until the amplification product is completely degraded.

As a second specific implementation of this example, the use method includes:
- an NAA reagent is placed in the second chamber 14 and an enzyme solution for degrading an NAA product is placed in the first chamber 13;
- the biochemical reaction test tube is inserted into an NAA instrument for temperature control, at which time, only the solution in the second chamber 14 is subjected to temperature conduction, and the solution in the first chamber 13 is not heated by a heating component of the NAA instrument;
- when the NAA reaction is completed, the biochemical reaction test tube is pulled out and placed upside down, such that the solutions in the first chamber 13 and the second chamber 14 are mixed; and
- the biochemical reaction test tube is placed upside down in an environment suitable for the degradation of the enzyme, and incubated until the amplification product is completely degraded.

As a third specific implementation of this example, the use method includes:
- an NAA reagent is placed in the first chamber 13 and an enzyme solution for degrading an NAA product is placed in the second chamber 14;
- the biochemical reaction test tube is inserted into an NAA fluorescence detection instrument for temperature control, at which time, only the solution in the first chamber 13 is subjected to temperature conduction and undergoes an amplification reaction;
- when the NAA reaction is completed, the biochemical reaction test tube is pulled out and placed upside down, such that the solutions in the first chamber 13 and the second chamber 14 are mixed; and
- the biochemical reaction test tube is placed upside down in an environment suitable for the degradation of the enzyme, and incubated until the amplification product is completely degraded.

The above examples are merely preferred examples of the present disclosure, which are not intended to limit the implementation and protection scope of the present disclosure. It should be noted by those skilled in the art that all equivalent replacements and obvious changes made by using the description of the present disclosure and the content of the drawings should be included in the protection scope of the present disclosure.

What is claimed is:

1. A biochemical reaction test tube comprising:
   a tube portion; and
   a cover portion, wherein the tube portion comprises:
   a tube portion body comprising:
   a tube portion body outer wall;
   a tube portion body inner wall having a tube portion body inner wall circumferential surface;
   a first chamber having a first chamber top and a first chamber closed bottom;
   a second chamber having a second chamber top, a second chamber lower side, and a second chamber closed bottom spaced apart from the first chamber closed bottom by 3 mm or more;
   a limit unit including a limit unit top and disposed on the tube portion body outer wall wherein either (1) the second chamber closed bottom and the limit unit top are coplanar in a horizontal plane or (2) the limit unit is disposed on the second chamber lower side; and
   at least one first fitting member disposed on the tube portion body inner wall circumferential surface,
   wherein the cover portion comprises:
   a cover portion outer wall having a cover portion outer wall circumferential surface, and
   at least one second fitting member disposed on the cover portion outer wall circumferential surface,
   wherein the at least one second fitting member is connectable to the at least one first fitting member such that, when connected, the cover portion seals off the tube portion, and the first chamber top communicates with the second chamber top, and wherein, when the limit unit is subjected to contact conductive heating by a biochemical reaction instrument comprising a heat source, either (1) the first chamber or the second chamber contacts the heat source or (2) the first chamber or the second chamber transmits a relevant biochemical reaction signal to a biochemical reaction optical detection instrument, the relevant biochemical reaction signal originating from a first biochemical reaction solution in the first chamber or from a second biochemical reaction solution in the second chamber.

2. The biochemical reaction test tube according to claim 1, wherein the first chamber has a first chamber axis, a first chamber outer side and a first chamber inner side and the second chamber has a second chamber axis, wherein the second chamber is disposed on the first chamber outer side or the second chamber is disposed on the first chamber inner side or both and wherein the first chamber axis is collinear with or parallel to the second chamber axis.

3. The biochemical reaction test tube according to claim 1, wherein the limit unit at least partially surrounds the tube portion body outer wall.

4. The biochemical reaction test tube according to claim 1, wherein the tube portion has a tube portion axial direction, the cover portion has a cover portion axial direction and the at least one first fitting member comprises a plurality of first fitting members arranged along the tube portion axial direction; and wherein
the at least one second fitting member comprises a plurality of second fitting members arranged along the cover portion axial direction.

5. The biochemical reaction test tube according to claim 1, further comprising:
a connecting member including a connecting member first end and a connecting member second end, wherein the connecting member first end is connected to the tube portion and the connecting member second end is connected to the cover portion.

6. The biochemical reaction test tube according to claim 1, wherein the cover portion further comprises:
an auxiliary member disposed on the cover portion outer wall; and the auxiliary member is configured to protrude from the tube portion when the cover portion seals off the tube portion.

7. The biochemical reaction test tube according to claim 6, wherein the auxiliary member has a first thickness and cover portion includes a top having a second thickness such that the first thickness is smaller than the second thickness; or the first thickness is smaller than or equal to 0.4 mm or both.

8. The biochemical reaction test tube according to claim 1, wherein the cover portion comprises:
a hollow member disposed inside the cover portion in a penetrating manner and including a hollow member upper end and a hollow member lower end and comprising:
a first opening element disposed on the hollow member upper end; and
a second opening element disposed at hollow member lower end; and
a sealing member configured to seal off the hollow member and comprising:
a first sealing element configured to seal off the first opening element; and
a second sealing element configured to seal off the second opening element.

9. The biochemical reaction test tube according to claim 8, wherein, when the hollow member is sealed off by the sealing member, (1) the first sealing element does not contact the second sealing element or (2) the first sealing element destroys the second sealing element.

10. The biochemical reaction test tube according to claim 8, wherein the hollow member comprises:
a hollow member inner wall including a hollow member inner wall circumferential surface;
a third fitting member disposed on the hollow member inner wall circumferential surface; and wherein the sealing member comprises:
a first sealing element outer wall including a first sealing element outer wall circumferential surface;
a fourth fitting member provided on the first sealing element outer wall circumferential surface, wherein the third fitting member can be connected to the fourth fitting member such that the first sealing element seals off the first opening element.

11. The biochemical reaction test tube according to claim 1, wherein the first chamber closed bottom has a structure selected from the group consisting of a cylindrical structure or a conical structure.

12. The biochemical reaction test tube according to claim 11, wherein the cylindrical structure has a cylindrical structure top having a cylindrical structure top inner diameter between 1.5 mm and 8 mm or the conical structure has a conical structure top having a conical structure top inner diameter between 1.5 mm and 8 mm.

13. The biochemical reaction test tube according to claim 1, wherein the second chamber top has a chamber top inner diameter between 5 mm and 15 mm.

14. The biochemical reaction test tube according to claim 1, further comprising:
(1) a metal warm-bath instrument configured to subject a biochemical reaction solution in the biochemical reaction test tube to contact conductive heating; or
(2) a biochemical reaction optical detection instrument configured to acquire an optical signal of the biochemical reaction solution in the biochemical reaction test tube when the biochemical reaction test tube is subjected to contact conductive heating; or both.

15. The biochemical reaction test tube according to claim 1, wherein the second chamber closed bottom is disposed above the first chamber closed bottom when the biochemical reaction test tube is in an upright position.

16. The biochemical reaction test tube according to claim 1, wherein the second chamber top remains open when the tube portion is sealed off by the cover portion.

* * * * *